(12) United States Patent
Chen et al.

(10) Patent No.: US 9,321,818 B2
(45) Date of Patent: Apr. 26, 2016

(54) DERMCIDIN-DERIVED PEPTIDES FOR LUNG CANCER DIAGNOSTICS

(75) Inventors: Chung-Hsuan Chen, Taipei (TW); Wei-Chao Chang, Baihe Township (TW); Michael Hsiao, Taipei (TW); Ming-Shyan Huang, Kaohsiung (TW); Chih-Jen Yang, Kaohsiung (TW)

(73) Assignee: Academia Sinica, Taipei (TW)

( * ) Notice: Subject to any disclaimer, the term of this patent is extended or adjusted under 35 U.S.C. 154(b) by 279 days.

(21) Appl. No.: 12/703,102

(22) Filed: Feb. 9, 2010

(65) Prior Publication Data

US 2011/0195133 A1  Aug. 11, 2011

(51) Int. Cl.
| | |
|---|---|
| C12Q 1/00 | (2006.01) |
| C07K 14/47 | (2006.01) |
| A61K 31/7088 | (2006.01) |
| A61K 33/24 | (2006.01) |
| A61K 38/04 | (2006.01) |
| A61K 45/06 | (2006.01) |
| G01N 33/574 | (2006.01) |
| G01N 30/72 | (2006.01) |
| G01N 33/68 | (2006.01) |

(52) U.S. Cl.
CPC ......... *C07K 14/4723* (2013.01); *A61K 31/7088* (2013.01); *A61K 33/24* (2013.01); *A61K 38/04* (2013.01); *A61K 45/06* (2013.01); *G01N 33/57423* (2013.01); *G01N 33/57488* (2013.01); *G01N 30/72* (2013.01); *G01N 33/6851* (2013.01)

(58) Field of Classification Search
None
See application file for complete search history.

(56) References Cited

U.S. PATENT DOCUMENTS 7,510,842 B2 * 3/2009 Podust et al. .................. 435/7.1

OTHER PUBLICATIONS

Carpagnano et al., Oncology, 2004, 66:180-184.*
Schneider et al., J Chromatography B, 2010, 878: 201-206.*
Kurova et al., Olin. Chem. Lab. Med., 2009, 47(6): 706-712.*
Chang et al., 57th American Society for Mass Spectrometry Conference on Mass Spectrometry, Pennsylvania, May 31, 2009-Jun. 4, 2009, p. S9.*
Izquierdo, Cancer Gene Therapy, 2005, 12: 217-227.*
Shankar, JAMA, 2005, 293(11): 1367-73.*
Burnett et al., Chemistry & Biology, 2012, 19: 60-71.*

* cited by examiner

*Primary Examiner* — Hong Sang
(74) *Attorney, Agent, or Firm* — Shantanu Basu; Eckman Basu LLP

(57) ABSTRACT

Methods for diagnosis of non-small cell lung cancers by detection of endogenous peptides in exhaled breath condensate (EBC) are provided. Diagnostic peptides derived from dermcidin (DC) are provided. A specific dermcidin-derived peptide E-R11, having the sequence ENAGEDPGLAR (SEQ ID NO:2), is provided. E-R11 peptide levels in EBC, as measured by mass spectrometry (MS), are highly diagnostic of non-small cell lung cancers. A method for inhibiting growth of lung cancer cells by inhibiting DCD expression by RNA interference also is provided.

14 Claims, 13 Drawing Sheets

Figure 1

| | Gender | | Age | | E-R11 positive [1] | | | | |
|---|---|---|---|---|---|---|---|---|---|
| | | | | | | Cancer stage | | Sensitivity | Specificity |
| | Male | Female | Male | Female | non-cancer [2] | I-II | III-IV | (%) | (%) |
| Healthy | 8 | 4 | 40.4 | 55.5 | 0 (12) | | | | 100 |
| Non-carcinoma | | | | | | | | | |
| COPD | 11 | 0 | 71.2 | | 1 (11) | | | | 91 |
| Pneumonia | 8 | 6 | 51.6 | 48.0 | 2 (14) | | | | 86 |
| Carcinoma | | | | | | | | | |
| Small cell | 5 | 0 | 58.6 | | | | 0 (5) | 0 | |
| Squamous | 10 | 0 | 70.2 | | | 2 (3) | 3 (7) | 50 | |
| Adenocarcinoma | 16 | 18 | 59.6 | 61.5 | | 3 (5) | 17 (27) | 63 | |

[1] Using mass peak-area intensity $1.04 \times 10^5$ as a cut-off value for outcome measurement
[2] The number in brackets represents the case number Figure 2
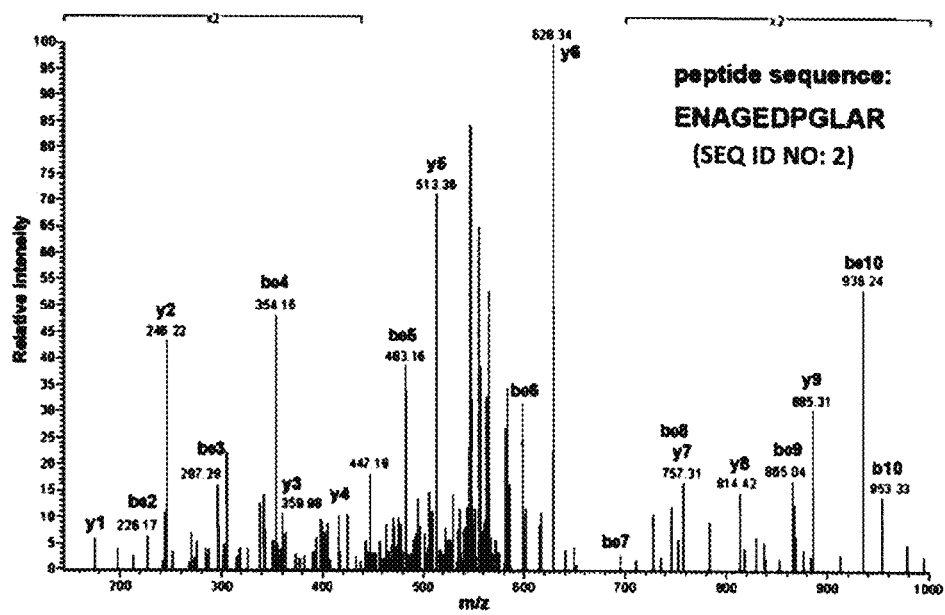
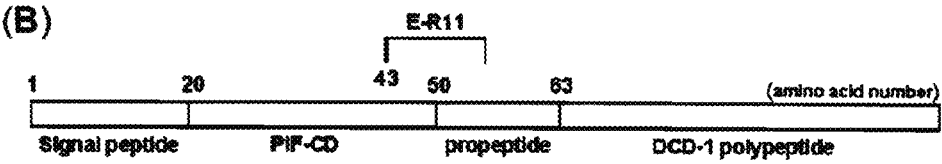

Figure 5

| Accession [a] | Protein name [b] |
|---|---|
| P35527 | Keratin, type I cytoskeletal 9 |
| P04264 | Keratin, type II cytoskeletal 1 |
| P02533 | Keratin, type I cytoskeletal 14 |
| P04259 | Keratin, type II cytoskeletal 6B |
| P13647 | Keratin, type II cytoskeletal 5 |
| P81605 | Dermcidin (DCD) |
| P04406 | Glyceraldehyde-3-phosphate dehydrogenase (GAPDH) |
| Q02413 | Desmoglein-1 |
| Q15517 | Corneodesmosin |
| P20930 | Filaggrin |
| Q08554 | Desmocollin-1 |
| P15924 | Desmoplakin |
| P06702 | Calgranulin B |
| P62328 | Thymosin β-4 |
| P06454 | Thymosin α-1 |
| P06733 | α-enolase |
| P02768 | Serum albumin |
| P12107 | Collagen α-1 |
| Q9NZT1 | Calmodulin-like protein 5 |
| P22626 | Heterogeneous nuclear ribonucleoproteins A2/B1 |

[a] Swiss-Port AC code.
[b] The deduced protein shows at least two matches in all EBC samples.

Figure 9-1

| Skin sample | 36-50 | E-R11 43-53 | 44-53 | 44-54 | 63-72 | 63-73 | 63-74 | 63-75 | 63-76 | 63-82 | 63-84 | 63-90 | 64-72 | 64-73 | 64-74 | 66-74 | 66-84 | 66-86 | 66-87 | 66-89 | 66-90 | 66-91 | 66-92 |
|---|---|---|---|---|---|---|---|---|---|---|---|---|---|---|---|---|---|---|---|---|---|---|---|
| Male 01 | | | | | 60 | 66 | 60 | 54 | 53 | 53 | | | 51 | 52 | 53 | | 68 | | | | 79 | | 62 |
| Male 02 | | 71 | | | | 56 | 56 | 55 | 50 | | 49 | | | | | | | | | | | | |
| Male 03 | | | | | 49 | 52 | 58 | 61 | | 58 | | | | | 53 | 50 | 55 | | | | 82 | 65 | |
| Male 04 | | 51 | | | 53 | 60 | 52 | | | | | | | | | 50 | | | | | | | |
| Male 05 | | | 60 | 64 | 59 | 61 | | 50 | | | | 65 | | | | | | | | | | | |
| Male 06 | | | | | | | | | | | | | | | | | | 59 | 70 | 64 | 75 | 66 | |
| Male 07 | | | | | | | | | | | | | | | | | | 77 | 59 | 65 | 68 | 54 | |
| Male 08 | | 63 | | | 52 | 55 | 53 | | | | | | | | | | 52 | | 57 | 66 | 87 | 51 | |
| Male 09 | | | | | 52 | 54 | 53 | 54 | | | | 56 | | | | | | | | 59 | 72 | | |
| Male 10 | | 49 | | | | | | 51 | | | | | | | | | | | | | | 51 | |
| Female 11 | 67 | | | | | | | | | | | | | | | | | | | | | | |
| Female 12 | | 59 | | | | | | | | | | | | | | | | | | | | | |
| Female 13 | | | | | | | | | | | | | | | | | | | | | | | |
| Female 14 | | | | | | | | | | | | | | | | | | | | | | | |
| Female 15 | | | | | | | | | | | | | | | | | | | | | | | |
| Female 16 | | 57 | | | | | | | | | | | | | | | | | | | | | |
| Female 17 | | | | | | | | | | | | | | | | | | | | | | | |
| Female 18 | | | | | | | | | | | | | | | | | | | | | | | |
| Female 19 | | 57 | 52 | | | | | | | | | | | | | | | | | | | | |
| Female 20 | | 51 | | | | | | | | | | | | | | | | | | | | | |

DCD-1 fragments

Figure 9-4

DCD-1 fragments

| Skin sample | | 86-96 | 86-100 | 86-103 | 86-104 | 86-105 | 86-108 | 87-104 | 91-108 | 91-110 | 92-102 | 92-104 | 92-105 | 92-106 | 92-107 | 92-108 | 92-109 | 92-110 | 93-104 | 93-108 | 97-108 | 97-109 | 97-110 |
|---|---|---|---|---|---|---|---|---|---|---|---|---|---|---|---|---|---|---|---|---|---|---|---|
| Male | 01 | 70 | | 60 | 72 | | | | | | | | | | | | 81 | | | | | | 68 |
| Male | 02 | 75 | | | 57 | | | | 52 | | | | | | | | 69 | | | | 54 | 70 | |
| Male | 03 | 64 | | 52 | 57 | | 49 | | | | | | | | | | 79 | 64 | | | 62 | 69 | 67 |
| Male | 04 | 70 | | 59 | | 50 | | | 66 | | | | | 55 | 80 | | | | | | 59 | 67 | |
| Male | 05 | 73 | | | 67 | | | 55 | 64 | 51 | 57 | 51 | 53 | 63 | 62 | 69 | | | 63 | | 63 | 64 | 55 |
| Male | 06 | | | | | | | | | | 60 | | 62 | 59 | 58 | 62 | 61 | | | 60 | 70 | | 71 |
| Male | 07 | | | | | | 53 | | | | 56 | 50 | 63 | 56 | 81 | 72 | 82 | | 63 | | 66 | 58 | |
| Male | 08 | 74 | | | 70 | | 51 | | | | | | | 58 | 71 | 69 | 77 | 49 | | | 68 | | |
| Male | 09 | 67 | 79 | | | | | | | | 55 | | 73 | 50 | 68 | 85 | 73 | 55 | 51 | 54 | 70 | | |
| Male | 10 | 53 | | | | | | | | | | | 77 | 51 | 65 | 74 | 83 | 53 | | | 57 | | |
| Female | 11 | 66 | | | | | | | | | | | | 59 | | 66 | | 52 | | | 61 | | |
| Female | 12 | | | | | | | | | | | | | | 57 | 67 | | | | | | | |
| Female | 13 | | | | | | | | | | | | | | | | | | | | | | |
| Female | 14 | 59 | | | | | | | | | | | | | | | | | | | 51 | | |
| Female | 15 | | | | | | | | | | | | | | | | | | | | 62 | | |
| Female | 16 | | | | | | | | | | | | | | | | | | | | 50 | | |
| Female | 17 | 62 | | | | | | | | | | | | | | | | | | | 60 | | |
| Female | 18 | | | | | | | | | | | | | | | | | | | | 52 | | |
| Female | 19 | | | | | | | | | | | | | | | | | | | | 53 | | |
| Female | 20 | | | | | | | | | | | | | | | | | | | | 66 | | |

DERMCIDIN-DERIVED PEPTIDES FOR LUNG CANCER DIAGNOSTICS

TECHNICAL FIELD OF THE INVENTION

The present invention relates to methods for detection and diagnosis of cancer, specifically lung cancer. Specifically, the invention relates to methods for diagnosing lung cancer using biomarkers derived from dermcidin and related peptides. More specifically, the invention relates to detection of dermcidin and related peptides in exhaled breath condensate.

SEQUENCE LISTING

This application includes a Sequence Listing submitted herewith via EFS-Web as an ASCII file created on Feb. 8, 2010, named SEQ_LIST_ASN50601US.txt, which is 1,898 bytes in size, and is hereby incorporated by reference in its entirety.

BACKGROUND OF THE INVENTION

Lung cancer is the most common cancer and the leading cause of cancer-related deaths worldwide (Ezzati M, et al. Lancet 2003; 362:847-52). More than 1.4 million people die of lung cancer each year (Jemal A, et al. CA Cancer J Clin 2008; 58:71-96.). Lung cancer is also the first frequently diagnosed cancer in Taiwan, and it accounts for 20% cancer deaths (Sinchaikul S, et al. Chang Gung Med J 2008; 31:417-30.). In the United States, it is estimated that 219,440 men and women (116,090 men and 103,350 women) were diagnosed with, and 159,390 men and women died of, cancer of the lung and bronchus in 2009 (Surveillance Research Program, National Cancer Institute. seer.cancer.gov/faststats; accessed on Feb. 1, 2010)

Lung cancers, also known as bronchogenic carcinomas, are broadly classified clinically into two types: small cell lung cancers (SCLC) and non-small cell lung cancers (NSCLC). This classification is based upon the microscopic appearance of the tumor cells themselves. These two types of cancers grow and spread in different ways and may have different treatment options.

SCLC comprise about 20% of lung cancers and are the most aggressive and rapidly growing of all lung cancers. SCLC are strongly related to cigarette smoking, with only 1% of these tumors occurring in nonsmokers. SCLC metastasize rapidly to many sites within the body and are most often discovered after they have spread extensively. Referring to a specific cell appearance often seen when examining samples of SCLC under the microscope, these cancers are sometimes called oat cell carcinomas.

NSCLC are the most common lung cancers, accounting for about 80% of all lung cancers. NSCLC can be divided into three main types that are named based upon the type of cells found in the tumor: (i) Adenocarcinomas are the most commonly seen type of NSCLC in the U.S. and comprise up to 50% of NSCLC. While adenocarcinomas are associated with smoking, like other lung cancers, this type is observed as well in nonsmokers who develop lung cancer. Most adenocarcinomas arise in the outer, or peripheral, areas of the lungs. Bronchioloalveolar carcinoma is a subtype of adenocarcinoma that frequently develops at multiple sites in the lungs and spreads along the preexisting alveolar walls. (ii) Squamous cell carcinomas were formerly more common than adenocarcinomas; at present, they account for about 30% of NSCLC. Also known as epidermoid carcinomas, squamous cell cancers arise most frequently in the central chest area in the bronchi. (iii) Large cell carcinomas, sometimes referred to as undifferentiated carcinomas, are the least common type of NSCLC. (iv) Mixtures of different types of NSCLC is also seen.

Regardless of histopathologic subtype, the 5-year survival rate for lung cancer is 10-15%, which is the lowest among all cancers (Hoffman P C, et al. Lancet 2000; 355:479-85). This is mainly due to more than 60% of the patients diagnosed with advanced or metastatic disease, reflecting the need for a better understanding of the mechanisms that underlie lung carcinogenesis (Granville C A, et al. Am J Respir Cell Mol Biol 2005; 32:169-76.). Surgical treatment remains the main treatment modality for lung cancer, but it is possible only for people who are diagnosed at an early stage of cancer. Surgical candidates diagnosed with stage I NSCLC have 5-year relative survival rates of 52% (Reed M F, et al. Am J Surg 2004; 188:598-602) that is significantly better than the expensive chemotherapy to increase the median survival to be in the range of only two to four months. Therefore, the early diagnosis of lung cancer is critical for life span and successful therapy.

Typical diagnosis of lung cancer combines x-ray with sputum cytology. Unfortunately, by the time a patient seeks medical attention for their symptoms, the cancer is at such an advanced state it is usually incurable. Consequently, research has been focused on early detection of tumor markers before the cancer becomes clinically apparent and while the cancer is still localized and amenable to therapy.

Classical screening procedures, such as chest radiography and sputum cytology, have not decreased the mortality of lung cancer (Humphrey L L, et al. Ann Intern Med 2004; 140:740-53). Spiral computed tomography with multitrack scanners and autofluorescence bronchoscopy offers high sensitivity to detect lung cancer, even at the pre-invasive stage (Gohagan J K, et al. Lung Cancer 2005; 47:9-15, McWilliams A, et al. Curr Opin Pulm Med 2005; 11:272-7). However, low specificity and expensive cost could be serious issues with this method. Serum biomarkers have emerged as potential targets for progression monitoring of lung cancer, yet current biomarkers have not been adequately validated as an effective clinical tool for early screening and diagnosis (Sung H J, et al. BMB Rep 2008; 41:615-25). There is an emergent need for valid diagnostic procedures aimed at screening lung cancer at an early stage. Breath analysis, an easily and non-invasive technique, is one of the most desirable methods to identify new biomarkers for lung cancer.

Exhaled breath comprises volatile compounds and non-volatile compounds. The volatile compounds include gaseous molecules, such as carbon monoxide, nitric oxide, alkanes and benzene derivatives (Pauling L, et al. Proc Natl Acad Sci USA 1971; 68:2374-6, Gordon S M, et al. Clin Chem 1985; 31:1278-82). Volatile organic compounds (VOCs) of exhaled breath frequently served as analytes for clinical assay and several VOCs were identified as biomarkers for lung diseases (Kharitonov S A, et al. Chest 2006; 130:1541-6, Koutsokera A, et al. Curr Med Chem 2008; 15:620-30). In addition, VOCs were also applied to the diagnosis of lung cancer and to follow up the prognosis of tumor resection (Poli D, et al. Respir Res 2005; 6:71, Phillips M, et al. Cancer Biomark 2007; 3:95-109, Poli D, et al. Acta Biomed 2008; 79 Suppl 1:64-72.). The non-volatile compounds include small molecules, such as nitrites, nitrates and hydrogen peroxide, and larger molecules, such as eicosanoids, proteins, and DNA (Mutlu G M, et al. Am J Respir Crit Care Med 2001; 164:731-7, Montuschi P, et al. J Allergy Clin Immunol 2002; 109:615-20, Shahid S K, et al. Am J Respir Crit Care Med 2002; 165:1290-3.). Exhaled breath condensate (EBC) can be collected by guiding and cooling exhaled air in a condenser system. EBC has been used to measure and detect various inflammatory airway diseases, including bronchial asthma, cystic fibrosis and COPD (Carpagnano G E, et al. Chest 2004; 125:2005-10, Liu J, et al. Respiration 2007; 74:617-23, Robroeks C M, et al. Pediatr Allergy Immunol 2008; 19:652-9, Samitas K, et al. Respir Med 2009; 103:750-6.). Compared with other respiratory conditions, there are relatively small numbers of studies focused on lung cancer using EBC (Dalayeris E, et al. Lung Cancer 2009; 64:219-25, Chan H P, et al. Lung Cancer 2009; 63:164-8.). Therefore, this is a potential field for more studies to investigate the tumorigenesis processes and identify new biomarkers in the airway.

Identification of antigens associated with the lung cancer proteome has been of particular interest. These antigens have been used in screening, diagnosis, clinical management, and potential treatment of lung cancer. For example, carcinoembryonic antigen (CEA) has been used as a tumor marker of several cancers, including lung cancer. (Nutini, et al. 1990. Int J Biol Markers 5:198-202). Squamous cell carcinoma antigen (SCC) is another established serum marker. (Margolis, et al. 1994. Cancer 73:605-609.). Other serum antigens for lung cancer include antigens recognized by monoclonal antibodies (MAb) 5E8, 5C7, and 1F10, the combination of which distinguishes between patients with lung cancer from those without. (Schepart, et al. 1988. Am Rev Respir Dis 138:1434-8). Serum CA 125, initially described as an ovarian cancer-associated antigen, has been investigated for its use as a prognostic factor in lung cancer. (Diez, et al. 1994. Cancer 73:136876). Other tumor markers studied for utilization in multiple biomarker assays for lung cancer include carbohydrate antigen CA19-9, neuron specific enolase (NSE), tissue polypeptide antigen (TPA), alpha fetoprotein (AFP), HCG beta subunit, and LDH. (Mizushima, et al. 1990. Oncology 47:43-48; Lombardi, et al. 1990. Chest 97:639-644; and Buccheri, et al. 1986. Cancer 57:2389-2396).

Monoclonal antibodies to the antigens associated with lung cancer have been generated and examined as possible diagnostic and/or prognostic tools. For example, monoclonal antibodies for lung cancer were first developed to distinguish non-small cell lung carcinoma (NSCLC) which includes squamous, adenocarcinoma, and large cell carcinomas from small cell lung carcinomas (SCLC). (Mulshine, et al. 1983. J Immunol 121:497-502). Other antibodies have also been developed as immunocytochemical stains for sputum samples to predict the progression of lung cancer. (Tockman, et al. 1988. J Clin Oncol 6:1685-1693). U.S. Pat. No. 4,816,402 discloses a murine hybridoma monoclonal antibody for determining bronchopulmonary carcinomas and possibly adenocarcinomas. Some monoclonal antibodies utilized in immunohistochemical studies of lung carcinomas include MCA 44-3A6, L45, L20, SLC454, L6, and YH206. (Radosevich, et al. 1985. Cancer Res 45:5808-5812).

In U.S. Pat. Nos. 5,589,579 and 5,773,579, a lung cancer marker antigen specific for non-small cell lung carcinoma was identified and designated LCGA (also known as HCAVIII and HCAXII). U.S. Pat. No. 7,569,662 and U.S. Pat. App. Pub. No. 2009/0204334 disclose biomarkers for lung cancer. However, despite the numerous examples of isolated lung cancer antigens and subsequent production of MAb to these antigens, none has yet emerged that has changed clinical practice. Thus far, the immunoassays developed have failed to meet the need for early detection. Overall, despite the identification and extensive study of several potential tumor markers, none has been found to have clinical utility as a diagnostic marker or screening tool for lung cancer. It seems probable that given the complexity of the genetic and molecular alterations that occur in lung cancer cells, the expression pattern of these complex changes may hold more vital information in screening, diagnosis and prognosis than the individual molecular changes themselves.

Proteolysis-inducing factor/dermcidin (PIF/DCD) is a novel human gene, located on chromosome 12, locus 12q13.1, that encodes a secreted 110-amino acid protein. Two transcripts for the protein have been identified in normal skin, breast, placenta and brain, and in various primary and metastatic tumor cells. (Majczak, G., et al., Genet. Mol. Res. 6 (4):1000-1011 (2007)). DCD was originally identified as an antimicrobial peptide secreted by sweat glands (Schittek B, et al. Nat Immunol 2001; 2:1133-7). In addition to its antimicrobial function, DCD acts as a survival-promoting factor by means of enhancing cell growth during tumorigenesis in breast carcinoma (Porter D, et al. Proc Natl Acad Sci USA 2003; 100:10931-6) as well as in hepatic carcinoma (Lowrie A G, et al. Br J Cancer 2006; 94:1663-71) and prostate cancer cells (Stewart G D, et al. Prostate 2007; 67:1308-17). Moreover, PIF-CD is reported to induce skeletal muscle proteolysis, causing cancer cachexia (Monitto C L, et al. Clin Cancer Res 2004; 10:5862-9, Lee Motoyama J P, et al. Biochem Biophys Res Commun 2007; 357:828-33). Dermcidin acts as a survival factor in a variety of cancer cell lines under hypoxia or oxidative stress. (Stewart G D, et al. Br J Cancer. 2008; 99(1):126-32.) Dermcidin has been shown to be among secretory proteins that are up-regulated stage-specifically with stage IA or IIIA non-metastatic lung adenocarcinoma. (Nishimura T. et al., J Proteomics. 2009 Nov. 27. [Epub ahead of print]).

Recent technological advances in proteomics have permitted the development of diagnostic tests for the detection of some cancers. For example, one such technology includes the ProteinChip® surface-enhanced laser desorption/ionization time of flight mass spectrometry (SELDI-TOF-MS) (Kuwata, H., et al., Biochem. Biophys. Res. Commun. 245:764-773 (1998); Merchant, M. et al., Electrophoresis 21:1164-1177 (2000)). This system uses surface-enhanced laser desorption/ionization time-of-flight (SELDI-TOF) mass spectrometry to detect proteins bound to a protein chip array. The SELDI system is an extremely sensitive and rapid method that analyzes complex mixtures of proteins and peptides. Applications of this technology show great potential for the early detection of prostate, breast, ovarian, bladder, and head and neck cancers (Li, J., et al., Clin. Chem. 48:1296-1304 (2002); Adam, B., et al., Cancer Res. 62:3609-3614 (2002); Cazares, L. H., et al., Clin. Cancer Res. 8:2541-2552 (2002); Petricoin, E. F., et al., Lancet 359:572-577 (2002); Petricoin, E. F. et al., J. Natl. Cancer Inst. 94:1576-1578 (2002); Vlahou, A., et al., Amer. J. Pathology 158:1491-1502 (2001); Wadsworth, J. T., et al., Arch. Otolaryngol. Head Neck Surg. 130:98-104 (2004). For example, PCT Patent Application No. WO/2005/034727 describes the use of SELDI ProteinChip® technology as a tool of interrogation for head and neck squamous cell carcinoma ("HNSCC") patients. This application describes how serum from HNSCC patients was compared to normal controls in order to develop HNSCC protein fingerprints for the diagnosis of HNSCC. However, to date, the use of SELDI had not been used to identify protein biomarkers for the detection of lung cancer.

Proteomic technologies have offered significant opportunities to discover clinical biomarkers (Kikuchi T, et al. Respirology 2007; 12:22-8). Mass spectrometry (MS) is one of the key tools of proteomic research to eliminate many of the limitations of traditional protein analyses. Also, tandem mass spectrometry (MS/MS) has become routine for peptides/proteins identification. The low-molecular-weight proteome, termed peptidome, provides a rich source of information for cancer diagnosis (Traub F, et al. Lab Invest. 2006; 86:246-53, Chang W C, et al. Proteomics Clin Appl 2008; 2:55-62.). Peptides, such as hormones, growth factors and cytokines, often possess specific functions in many physiological processes. The exploration of endogenous peptides, created by enzymatic cleavage of proteins in particular cellular environments, can result in relevant biomarker candidates (Petricoin E F, et al. Nat Rev Cancer 2006; 6:961-7, Schrader M, et al. Disease Markers 2006; 22:27-37). Coupling with low flow-rate capillary chromatography, the sensitivity of peptide detection by MS can reach attomole level (Amberoid R, et al. Nature 2003; 422:198-207), which holds great promise for biomolecular microanalysis. Furthermore, peptide sequence can be determined directly by MS/MS analysis without the need of sample manipulations, such as trypsin digestion. The identification of peptide marker is more convenient than conventional biomarker research.

Continued efforts to identify protein profiles or patterns that differentiate cancer from non-cancer could lead to earlier detection of lung cancer and the development of diagnostic tests for lung cancer. There is a need for methods and compositions for the diagnosis of lung cancer that are clinically useful.

SUMMARY OF THE INVENTION

This invention provides novel peptide markers that are differentially present in exhaled breath samples of patients with lung cancer and in the samples of control subjects. The present invention also provides sensitive methods and kits that can be used as an aid for the diagnosis of lung cancer by detecting these novel markers. The markers can be resolved from other proteins in a sample by, e.g., chromatographic separation coupled with mass spectrometry, or by traditional immunoassays. In preferred embodiments, the method of resolution involves Surface-Enhanced Laser Desorption/Ionization ("SELDI") mass spectrometry, in which the surface of the mass spectrometry probe comprises absorbents that bind to the marker.

The invention relates to the identification of peptide biomarkers for lung cancer using techniques such as MALDI-TOF, or nano-LC/LTQ-FTICR MS, or SELDI-TOF to assay exhaled breath condensate (EBC) samples, which were obtained from healthy subjects, pneumonia, chronic obstructive pulmonary disease (COPD), squamous carcinoma, adenocarcinoma, and small cell carcinoma patients. Peptides were quantified using a synthetic peptide for quantitative calibration. For validation, the expression of potential target in patients' tissues and cell lines was determined. Moreover, the biological effects of potential target on cancer cells were determined by silencing its gene expression.

This invention relates to dermcidin (DCD) protein having the amino acid sequence (UniProt Accession Code: P81605:

(SEQ ID NO: 1)
MRFMTLLFLTALAGALVCAYDPEAASAPGSGNPCHEASAAQKENAGEDPG

LARQAPKPRKQRSSLLEKGLDGAKKAVGGLGKLGKDAVEDLESVGKGAVH

DVKDVLDSVL.

This invention relates to E-R11, a peptide derived from dermcidin (DCD) having the amino acid sequence: ENAGEDPGLAR (SEQ ID NO: 2).

The invention relates to a method of using a peptide biomarker to diagnose lung cancer in a test subject, the method comprising: (a) providing a sample obtained from an exhaled breath condensate (EBC) of the test subject, wherein the EBC comprises the peptide biomarker; (b) detecting a level of the biomarker in the exhaled breath condensate-derived sample; (c) comparing the level of the biomarker in the EBC sample to a reference level of the biomarker; and (d) differentially diagnosing a presence or absence of lung cancer in the test subject as indicated by the comparison. In one aspect, differential diagnosis is an adjunct to a primary diagnostic method of testing said subject for carcinoma of the lung.

In one aspect, the lung cancer is a non-small cell lung carcinoma (NSCLC) comprising squamous cell carcinoma, large cell lung carcinoma or adenocarcinoma, or a combination thereof.

In one embodiment, the biomarker is a peptide comprising a partial sequence of dermcidin (DCD; SEQ ID NO: 1), wherein the peptide is formed by enzymatic digestion of dermcidin. In some embodiments the peptide comprises DCD sequences from the proteolysis-inducing factor-core peptide (PIF-CD) region of dermcidin.

In one embodiment, the biomarker is a peptide consisting essentially of the sequence of E-R11: ENAGEDPGLAR (SEQ ID NO: 2).

In one aspect, the level of the biomarker is detected by a method comprising mass spectrometry (MS). The mass spectrometry may be matrix-assisted laser desorption/ionization time-of-flight mass spectrometry (MALDI-TOF MS), or linear ion trap-Fourier transform ion cyclotron resonance mass spectrometry (LTQ-FTICR MS), or surface-enhanced laser desorption ionization mass spectrometry (SELDI-MS).

In one aspect, the sample comprises purified peptide constituents from EBC. In some embodiments, the peptide constituents from EBC are purified using copper-coated magnetic beads.

In one aspect, the reference level of the biomarker corresponds to the highest level of the biomarker in one or more healthy subjects. In one embodiment, the biomarker is E-R11, the biomarker level is detected by mass spectrometry and the biomarker level is measured as mass peak area intensity. In some embodiments, the biomarker level is measured as mass peak area intensity about $1.0 \times 10^5$.

In another aspect, the reference level of the biomarker corresponds to the highest level of the biomarker in one or more subjects without cancer. In one embodiment, the biomarker is E-R11, the biomarker level is detected by mass spectrometry and the biomarker level is measured as mass peak area intensity. In some embodiments, the biomarker level is measured as mass peak area intensity about $1.8 \times 10^5$.

In one aspect, the method further comprises monitoring the inhibition of lung cancer growth following administration of a chemotherapeutic regimen, a surgical resection or a photodynamic therapy to the test subject. In some embodiments, the chemotherapeutic regimen comprises a therapeutic dose of one or more of Cisplatin, Etoposide, Carboplatin, Paclitaxel, Docetaxel, Vinorelbine, Doxorubicin, Vincristine, Ifosfamide, and Gemcitabine.

The invention relates to a peptide consisting essentially of the sequence of E-R11: ENAGEDPGLAR (SEQ ID NO: 2), and functional variants thereof. In one aspect, the peptide is synthetically produced. In one aspect, the peptide is provided in a sample for analysis by mass spectrometry. In one embodiment, the peptide comprises a kit for diagnosis of NSCLC.

The invention relates to a method for inhibiting growth of lung cancer cells, the method comprising: administering to the cells an amount of an inhibitory agent sufficient for altering dermcidin (DCD) expression or activity in the cell. In one aspect, the lung cancer cells are in a human subject. In some aspects, the lung cancer is a non-small cell lung carcinoma (NSCLC) comprising squamous cell carcinoma, or adenocarcinoma, or large cell lung carcinoma, or any combination thereof.

In one aspect, the inhibitory agent comprises an oligonucleotide that functions via RNA interference. In some embodiments, the oligonucleotide is selected from the group consisting of an antisense oligonucleotide, a siRNA, and a shRNA. In some embodiments, the oligonucleotide comprises a pharmaceutical composition.

In one aspect, the method further comprises administering a chemotherapeutic regimen, a surgical resection or a photodynamic therapy to the subject. In one embodiment, the chemotherapeutic regimen comprises a therapeutic dose of one or more of Cisplatin, Etoposide, Carboplatin, Paclitaxel, Docetaxel, Vinorelbine, Doxorubicin, Vincristine, Ifosfamide, and Gemcitabine.

These and other aspects will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 1 shows characteristics of patients tested and diagnosed by E-R11 analysis.

FIGS. 2A-2B show MS/MS spectrum of E-R11 and the peptide subunits map of DCD. (FIG. 2A) The E-R11 sequence and MS/MS spectrum with b ion and y ion fragments were shown. (FIG. 2B) The unprocessed DCD has 110 amino acids and comprises four polypeptides. The number represents the amino acid position relative to the start residue of DCD. E-R11 sequence corresponds to amino acid 43-amino acid 53 in the DCD sequence.

FIG. 5 shows a list of proteins deduced from peptides identified in EBC.

FIGS. 9-1 through 9-4 show dermcidin peptide analysis of skin extracts. Skin extracts coming from twenty subjects were analyzed by nano LC-LTQ FTICR MS. Most of identified peptides were DCD-1 fragments. E-R11, with amino acid sequence of residues 43 through 53, is shown in RED. The italicized number represents the amino acid sequence of dermcidin. The number in the brackets represents the top peptide score at all matches of unique sequence. The count of matches are shown by color filled in the brackets: white box (☐), gray box (■), green box (■), and brown box (■) show 1, 2, 3 and 4 times, respectively.

(FIG. 10A) The endogenous expression of DCD in tissues of lung squamous carcinoma and adenocarcinoma patients was determined by RT-PCR analysis. N, T showed paired samples. S26 signal as an internal control. (FIG. 10B) The infection efficiency of H520 and PC13 by DCD shRNA encoding lentivirus. (FIG. 10C) The knockdown effect of DCD shRNA in H520 and PC13. The expression levels of mRNA were determined by RT-qPCR. (FIG. 10D) The viability assay of lung normal and cancer cell lines after 72 hr infection with DCD shRNA containing lentivirus.

DETAILED DESCRIPTION OF THE INVENTION

Figure 3:
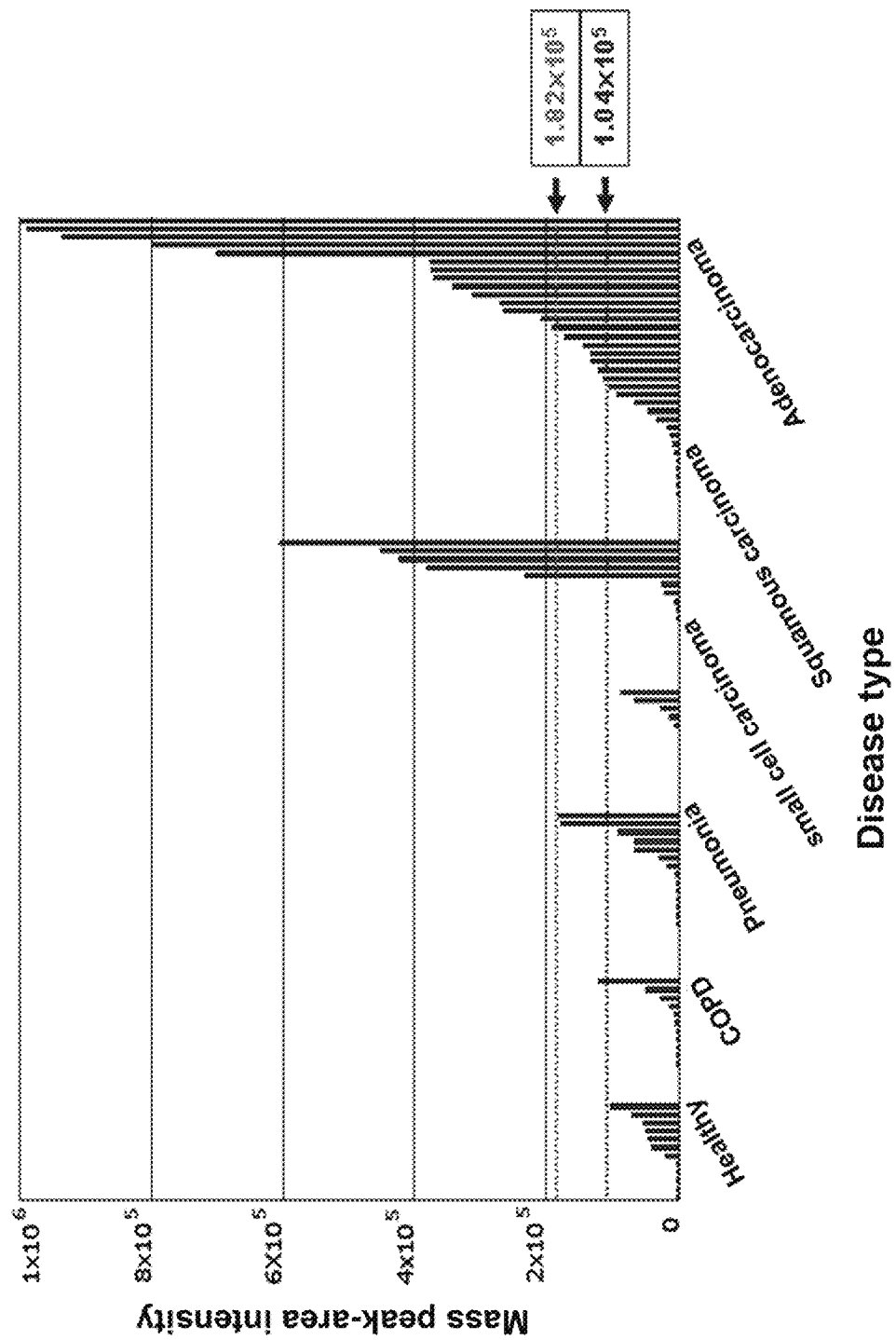
FIG. 3 shows expression of E-R11 in EBC of healthy subjects and various lung disease patients. The mass peak-area intensity of E-R11 in individual EBC was measured. The line of intensity $1.04 \times 10^5$ represented the maximum value of E-R11 detected in the healthy subject group. Another line of intensity $1.82 \times 10^5$ represented the maximum value of E-R11 detected in all non-cancer groups.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

DEFINITIONS

A "marker" is a gene or protein which may be altered, wherein said alteration is associated with cancer. The alteration may be in amount, structure, and/or activity in a cancer tissue or cancer cell, as compared to its amount, structure, and/or activity, in a normal or healthy tissue or cell (e.g., a control), and is associated with a disease state, such as cancer. For example, a marker of the invention which is associated with cancer may have altered copy number, expression level, protein level, or protein activity in a cancer tissue or cancer cell as compared to a normal, healthy tissue or cell.

The term "peptide" is intended to indicate a sequence of two or more amino acids joined by peptide bonds, wherein said amino acids may be natural or unnatural. The term encompasses the terms polypeptides and proteins, which may consists of two or more polypeptides held together by covalent interactions, such as for instance cysteine bridges, or non-covalent interactions. It is to be understood that the term is also intended to include peptides, which have been derivatized, for instance by the attachment of lipophilic groups, PEG or prosthetic groups. The term peptide includes any suitable peptide and may be used synonymously with the terms polypeptide and protein, unless otherwise stated or contradicted by context; provided that the reader recognize that each type of respective amino acid polymer-containing molecule may be associated with significant differences and thereby form individual embodiments of the present invention (for example, a peptide such as an antibody, which is composed of multiple polypeptide chains, is significantly different from, for example, a single chain antibody, a peptide immunoadhesin, or single chain immunogenic peptide). Therefore, the term peptide herein should generally be understood as referring to any suitable peptide of any suitable size and composition (with respect to the number of amino acids and number of associated chains in a protein molecule). Moreover, peptides in the context of the inventive methods and compositions described herein may comprise non-naturally occurring and/or non-L amino acid residues, unless otherwise stated. In one embodiment, a peptide according to the invention comprises at least 70%, 75%, 80%, 85%, 90%, or 95% identity with the sequence ENAGEDPGLAR (SEQ ID NO: 2).

The term "altered amount" of a marker or "altered level" of a marker refers to increased or decreased copy number of a marker or peptide level, e.g., E-R11, and/or increased or decreased expression level of a particular marker gene or genes in a cancer sample, as compared to the expression level or copy number of the marker in a control sample. The term "altered amount" of a marker also includes an increased or decreased protein level of a marker in a sample, e.g., a cancer sample, as compared to the protein level of the marker in a normal, control sample.

The amount of a marker, e.g., expression or copy number of a marker or DCD or E-R11, or protein level of a marker, in a subject is "significantly" higher or lower than the normal amount of a marker or DCD or E-R11, if the amount of the marker is greater or less, respectively, than the normal level by an amount greater than the standard error of the assay employed to assess amount, and preferably at least twice, and more preferably three, four, five, ten or more times that amount. Alternately, the amount of the marker or MCR in the subject can be considered "significantly" higher or lower than the normal amount if the amount is at least about two, and preferably at least about three, four, or five times, higher or lower, respectively, than the normal amount of the marker or DCD or E-R11.

The term "altered level of expression" of a marker or DCD or E-R11 refers to an expression level of a marker in a test sample e.g., a sample derived from a patient suffering from cancer, that is greater or less than the standard error of the assay employed to assess expression or copy number, and is preferably at least twice, and more preferably three, four, five or ten or more times the expression level or copy number of the marker or DCD or E-R11 in a control sample (e.g., sample from a healthy subjects not having the associated disease) and preferably, the average expression level or copy number of the marker or DCD or E-R11 in several control samples. The altered level of expression is greater or less than the standard error of the assay employed to assess expression or copy number, and is preferably at least twice, and more preferably three, four, five or ten or more times the expression level or copy number of the marker or DCD or E-R11 in a control sample (e.g., sample from a healthy subjects not having the associated disease) and preferably, the average expression level or copy number of the marker or DCD or E-R11 in several control samples.

An "overexpression" or "significantly higher level of expression" of a marker or DCD or E-R11 refers to an expression level in a test sample that is greater than the standard error of the assay employed to assess expression, and is preferably at least twice, and more preferably three, four, five or ten or more times the expression level of the marker or DCD or E-R11 in a control sample (e.g., sample from a healthy subject not afflicted with cancer) and preferably, the average expression level of the marker or DCD or E-R11 in several control samples.

An "RNA interfering agent" as used herein, is defined as any agent that interferes with or inhibits expression of a target gene, e.g., a marker of the invention, by RNA interference (RNAi). Such RNA interfering agents include, but are not limited to, nucleic acid molecules including RNA molecules which are homologous to the target gene, e.g., a marker of the invention, or a fragment thereof, short interfering RNA (siRNA), and small molecules which interfere with or inhibit expression of a target gene by RNA interference (RNAi).

"RNA interference (RNAi)" is an evolutionarily conserved process whereby the expression or introduction of RNA of a sequence that is identical or highly similar to a target gene results in the sequence specific degradation or specific post-transcriptional gene silencing (PTGS) of messenger RNA (mRNA) transcribed from that targeted gene (see Coburn, G. and Cullen, B. (2002) J of Virology 76(18):9225), thereby inhibiting expression of the target gene. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target genes. As used herein, "inhibition of target gene expression" or "inhibition of marker gene expression" includes any decrease in expression or protein activity or level of the target gene (e.g., a marker gene of the invention) or protein encoded by the target gene, e.g., a marker protein of the invention. The decrease may be of at least 30%, 40%, 50%, 60%, 70%, 80%, 90%, 95% or 99% or more as compared to the expression of a target gene or the activity or level of the protein encoded by a target gene which has not been targeted by an RNA interfering agent.

"Short interfering RNA" (siRNA), also referred to herein as "small interfering RNA" is defined as an agent which functions to inhibit expression of a target gene, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the over hang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) RNA April; 9(4):493-501).

RNA interfering agents, e.g., siRNA molecules, may be administered to a patient having or at risk for having cancer, to inhibit expression of a marker gene of the invention, e.g., a marker gene which is overexpressed in cancer (such as the markers listed in FIG. 5) and thereby treat, prevent, or inhibit cancer in the subject.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "transcribed polynucleotide" is a polynucleotide (e.g. an RNA, a cDNA, or an analog of one of an RNA or cDNA) which is complementary to or homologous with all or a portion of a mature RNA made by transcription of a marker of the invention and normal post-transcriptional processing (e.g. splicing), if any, of the transcript, and reverse transcription of the transcript.

"Complementary" refers to the broad concept of sequence complementarity between regions of two nucleic acid strands or between two regions of the same nucleic acid strand. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantial homology," as used herein, refers to homology of at least 50%, more preferably, 60%, 70%, 80%, 90%, 95% or more.

Detection of E-R11 in Exhaled Breath Concentrate

Exhaled breath condensate (EBC) analysis is a simple and truly non-intrusive approach to acquire information on understanding airway inflammation and other diseases of the respiratory system such as tumorigenesis (Koutsokera A, et al. Curr Med Chem 2008; 15:620-30, Dalayeris E, et al. Lung Cancer 2009; 64:219-25, Chan H P, et al. Lung Cancer 2009; 63:164-8.) There are several striking advantages to utilize breath testing for screening purposes: (a) it does not influence airway function or cause inflammation (Carpagnano G E, et al. Chest 2004; 125:2005-10); (b) it can be performed repeatedly within short intervals (Liu J, et al. Respiration 2007; 74:617-23); (c) it is not significantly affected by age, gender or disease status (Liu J, et al. Respiration 2007; 74:617-23); and (d) it can be considered as a lung-specific analytic approach.

Cancer cells have distinct properties from normal cells that they may synthesize new proteins or change the protein expression levels during tumorigenesis (Watkins S J, et al. Br. J. Cancer 2002; 86:1023-1027). A number of soluble components of the lung exist in the epithelial lining fluid of alveoli (Sabounchi-Schütt F, et al. *Eur Respir J* 2003; 21:414-420), therefore the secreted new synthetic proteins can be digested into peptides under enzymatic processes. Subsequently, the small peptides have the possibility of adding to exhaled breath like other EBC compounds. The exploration of endogenous peptides, created by enzymatic cleavage of proteins in particular cellular environments, can result in relevant biomarker candidates (Chang W C, et al. Proteomics Clin Appl 2008; 2:55-62, Petricoin E F, et al. Nat Rev Cancer 2006; 6:961-7.) However, trace amounts of materials in EBC makes detection a challenging task. This invention is based on determination of the peptidome of EBC in search of potential biomarkers for lung cancer diagnosis.

Patients with histological evidence of primary lung cancer were enrolled in a study. Specifically, squamous cell carcinoma, adenocarcinoma, small cell carcinoma, pneumonia, chronic obstructive pulmonary disease (COPD), and healthy subjects were enrolled (FIG. 1). The inclusion criteria included patients with newly diagnosed lung cancer before treatment. The diagnosis of lung cancer was confirmed by histological examinations of biopsy and/or cytology specimens obtained during fiber-optic bronchoscopy or with CTguided trans-thoracic needle aspiration biopsy. Stage of lung cancer was determined according to the staging system of American Joint Committee on Cancer (AJCC) TNM classification. The early stage of lung cancer indicated stage I, II or IIIA. The late or advanced stage of lung cancer indicated stage IIIB and stage IV. Informed consent was obtained from each participant (over 18 years old) before enrollment in the study.

The control group of the study included subjects without lung cancer, matched for socioeconomic and age group, and comprised nonsmokers, smokers, and ex-smokers, defined as not having smoked for at least 1 year. They were healthy or had pneumonia, chronic obstructive pulmonary disease (COPD) during hospitalization. (FIG. 1). The exclusion criteria included: (i) patients who refused to enter this study; (ii) patients with lung cancer but who had experienced chemotherapy or radiotherapy; (iii) patients with pulmonary tuberculosis; (iv) patients with unclassified non-small cell carcinoma; (v) patients with other solid or hematological malignancy and (vi) patients with lung cancer but cannot open his mouth because of betel chewing or oral diseases.

The number of patients in each category and their ages and disease stages are listed in FIG. 1. EBC collection was performed by using an EcoScreen condenser. Metal affinity copper magnetic beads were used to purify EBC before MS analysis.

Pattern comparison of MS spectra is a convenient method to explore biomarkers from peptide pools. The polymer contaminants, coming from trace amounts of detergent and the polypropylene collector of EcoScreen condenser, have interfered with such kind of approaches. These contaminants perhaps produce no effects on the traditional VOCs and protein analysis of EBC, but it is a serious issue for peptidomic investigations. Thus, improving condenser materials for removing contaminant resources is critical for the extensive peptidomic studies. In this work, we effectively reduced the polymer impurities by using the metal-affinity copper magnetic beads to purify EBC samples. Moreover, LTQ-FT ICR MS was applied to analyze the peptide constituents of purified EBC and successfully detected peptides at attomole level.

Based on MS/MS analysis and the MASCOT search, approximately 20 to 100 peptides that were identified in each EBC sample, were deduced to be from fewer than 10 proteins. (FIG. 5). In addition to cytoplasmic proteins and nuclear proteins, most of the deduced proteins identified from EBC belong to the junctional complex of desmosome, which is a cellular structure specialized for cell-to-cell adhesion. The intracellular cytoskeletal filament molecules keratins were also identified. The results illustrated that the decomposition of epithelial cells is a common phenomenon, so these molecules can be detected at normal conditions and disease statuses. Keratins, ranging in concentration from ten to thirty microgram per milliliter (Jackson A S, et al. Am J Respir Crit Care Med 2007; 175:222-7), are the major proteins in EBC (Hoffmann H J, et al. Eur Respir J 2008; 31:380-4). We found the most abundant peptides identified as keratin fragments that is in agreement with the observation of keratin proteins. Some deduced proteins were identified as potential cancer-related biomarkers at the previous studies, including cal-granulin B (Arai K, et al. Oncol Rep 2001; 8:591-6, Hiratsuka S, et al. Nat Cell Biol 2006; 8:1369-75), thymosin β-4 (Ji P, et al. Oncogene 2003; 22:8031-41, Cha H J, et al. J Natl Cancer Inst 2003; 95:1674-80) and α-enolase (Chang G C, et al. Clin Cancer Res 2006; 12:5746-54, Li C, et al. Proteomics 2006; 6:547-58). Due to lack of reproducibility in various groups of EBC, their roles in the tumorigenesis of lung cancer were not confirmed.

A total of twenty types of predicted proteins were found in all EBC samples. Among the identified peptides, the most abundant peptides were the fragments of keratin type I cytoskeletal 9 and type II cytoskeletal 1 proteins. The mass peak-area intensities of the relative peptides of both proteins showed no difference in the various groups of EBC. The most commonly identified peptides did not show a consistent expression pattern across a specific disease type or in every EBC sample. The dermcidin (DCD)-derived peptide was the sole exception.

Dermcidin (DCD) has 110 amino acids and comprises a signal peptide, a proteolysis-inducing factor-core peptide (PIF-CD), a propeptide and a skim antimicrobial peptide DCD-1 (FIG. 2B). The E-R11 tryptic peptide overlaps part of PIF-CD and the propeptide. DCD was originally identified as an antimicrobial peptide secreted by sweat glands (Schittek B, et al. Nat Immunol 2001; 2:1133-7). In addition to its antimicrobial function, DCD acts as a survival-promoting factor by means of enhancing cell growth during tumorigenesis in breast carcinoma (Porter D, et al. Proc Natl Acad Sci USA 2003; 100:10931-6) as well as in hepatic carcinoma (Lowrie A G, et al. Br J Cancer 2006; 94:1663-71) and prostate cancer cells (Stewart G D, et al. Prostate 2007; 67:1308-17). Moreover, PIF-CD is reported to induce skeletal muscle proteolysis, causing cancer cachexia (Monitto C L, et al. Clin Cancer Res 2004; 10:5862-9, Lee Motoyama J P, et al. Biochem Biophys Res Commun 2007; 357:828-33). As a candidate oncogene product, the expression of DCD in lung cancer cell is a reasonable speculation. Disclosed herein is the endogenous expression of DCD in tissues of squamous carcinoma and adenocarcinoma patients and in lung cancer cell lines by RT-PCR analysis. Further, the inhibition of DCD expression is associated with lung cancer cell viability.

The 564.76 m/z DCD-derived peptide with a charge state of +2 had a conspicuous MS/MS spectrum for sequence determination, which was ENAGEDPGLAR (SEQ ID NO:2) corresponding to amino acid residue numbers 43-53 (FIG. 2B) of dermcidin. E-R11 derives from the enzymatic digestion of DCD through the natural process of the human body.

Figure 4:
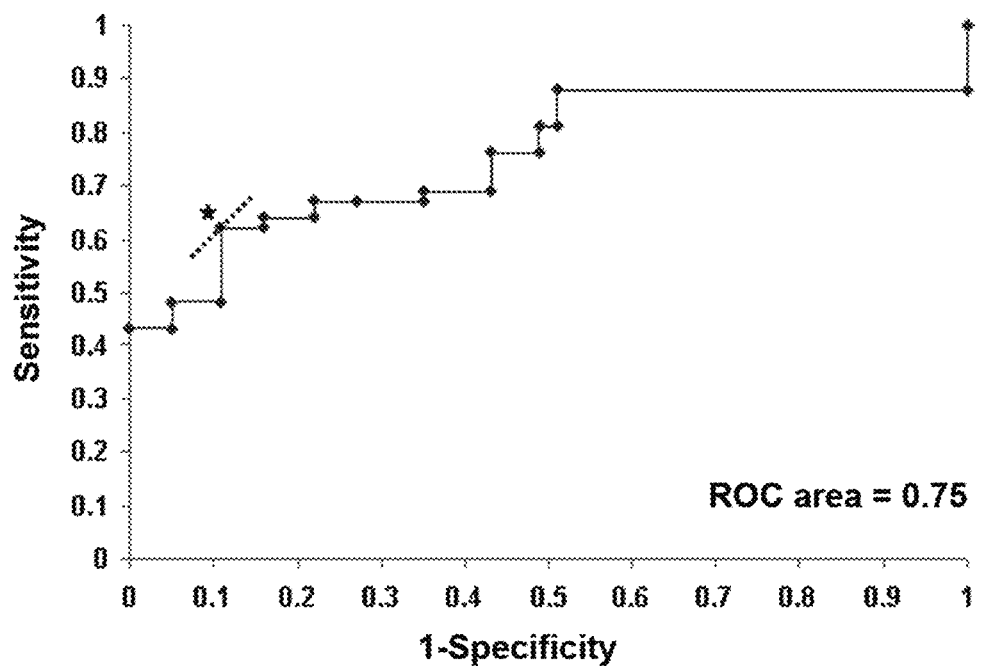
FIG. 4 shows ROC curve analysis of E-R11 for NSCLC diagnosis. The AUS was 0.75. The star sign, the optimal Youden index, showed the contact point of ROC curve with the tangent of slope 1.

The reproducibility of MS analysis was estimated by three repeated measurements of various groups of EBC samples. The average constant of variance (CV) values for health, squamous carcinoma and adenocarcinoma groups were 8.3%, 12.1% and 9%, respectively, and total average CV value was 9.6% for all measurements. The expression of E-R11 in every EBC sample showed that the non-small cell lung cancer (NSCLC) group including the squamous carcinoma and adenocarcinoma had higher levels of E-R11 than healthy, SCLC and the other respiratory disease groups (FIG. 3). The average mass peak-area intensities were $2.15 \times 10^5$ for squamous and $2.46 \times 10^5$ for adenocarcinoma, but only $3.21 \times 10^4$, $2.07 \times 10^4$, $4.54 \times 10^4$ and $4.06 \times 10^4$ for healthy subjects, COPD, pneumonia and small cell carcinoma, respectively. The value of the area under the curve (AUC) was 0.75, which illustrates that E-R11 had a fair to good diagnostic power (FIG. 4).

The diagnostic sensitivity and specificity show an optimum combination when the cut-off value of E-R11 mass peak-area intensity is approximately equal to $1 \times 10^5$. It is close to the value of the characteristic line with mass peak-area intensity of $1.04 \times 10^5$, which is the highest intensity of E-R11 in the healthy group (FIG. 3). With this cut-off threshold, all healthy people would not be diagnosed as NSCLC; however, a subset of COPD and pneumonia patients may have false diagnoses. The specificities for healthy subjects, COPD and pneumonia patients were 100%, 91% and 86%, respectively, and for all non-cancer groups the specificity was 92%. The sensitivities for squamous and adenocarcinoma patients were 50% and 63%, respectively, and 60% for all NSCLC groups. Using E-R11 for the diagnosis of NSCLC, the sensitivity and specificity show no notable difference between the early and late cancer stages. About 60% early stage NSCLC patients (squamous: 67% (2/3); adenocarcinoma: 60% (3/5)) can be diagnosed with cancer (FIG. 1). This suggests that E-R11 peptide possesses a valuable potential to serve as clinical biomarker for NSCLC early diagnosis. To measure E-R11 level in EBC, a synthetic peptide was used as a standard for quantitative calibration.

To validate DCD expression in lung cancer cells, the endogenous RNA expression of the DCD gene in lung cancer patient tissues and lung cancer cell line samples was determined. Two out of six squamous carcinoma and three out of six adenocarcinoma tissue samples showed DCD RNA expression by RT-PCR analysis. Most of the paired normal tissue samples were found to have either no or very weak DCD expression. Endogenous RNA expression of DCD was also found in the lung cancer cell lines H520 (squamous carcinoma) and PC13 (adenocarcinoma). The lung fibroblast cell line, WI-38, and the bronchial epithelial cell line, BEAS-2B, were found to have no endogenous DCD expression.

To characterize the biological activities of DCD in lung cancer cells, the functional consequences of DCD expression knockdown were determined by using short hairpin RNA (shRNA) delivered using a lentiviral vector. Real-time quantitative PCR was used to assay the knockdown of DCD. The results indicate that both the H520 and PC13 cell lines could be infected at a high efficiency with DCD shRNA lentiviruses and that DCD shRNA could significantly knockdown the endogenous RNA expression of DCD in H520 (~60%) and PC13 (~70%). Whether DCD expression knockdown resulted in growth reductions in normal or cancer cell lines was examined. The results showed 20 to 30 percents growth reductions in H520 and PC13 cells after DCD shRNA delivery, while no growth reduction in normal fibroblast and epithelial cells was observed. EBC analysis combined with MS technique is a valuable method for lung cancer screening. E-R11 serves as a biomarker for NSCLC diagnosis.

The increased levels of E-R11 reflect the biochemical changes of airway lining fluid and the physiological state of the lung in lung cancer. As disclosed herein, the consistent presence of E-R11 in patient's EBC can be regarded as an indicated target for monitoring lung cancer.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Patients and EBC Collection

EBC samples were collected from 47 patients with histological evidence of lung cancer—5 patients with small cell carcinoma, 10 patients with squamous cell carcinoma, and 32 patients with adenocarcinoma. 11 patients with chronic obstructive lung disease, 14 patients with pneumonia and 12 healthy subjects for the study were also enrolled. All subjects gave written, informed consent for this study.

An EcoScreen condenser (Erich Jaeger GmbH, Hoechberg, Germany) was used to collect EBC according to the manufacturer's instructions. Subjects did not eat one hour prior to EBC collection. Subjects were asked to breath at a normal frequency and tidal volume for 15 minutes, while wearing a nose clip. If they felt saliva in their mouth, they were instructed to swallow it. The exhaled air passed through a mouthpiece and a 2-way non-re-breathing valve, and then was frozen at −2° C. The condensates (more than 1 ml) were thawed and then transferred to 1.5 ml microtube (Axygen, Union, USA) and immediately stored at −70° C. until further analysis.

Example 2

EBC Purification

Figure 6:
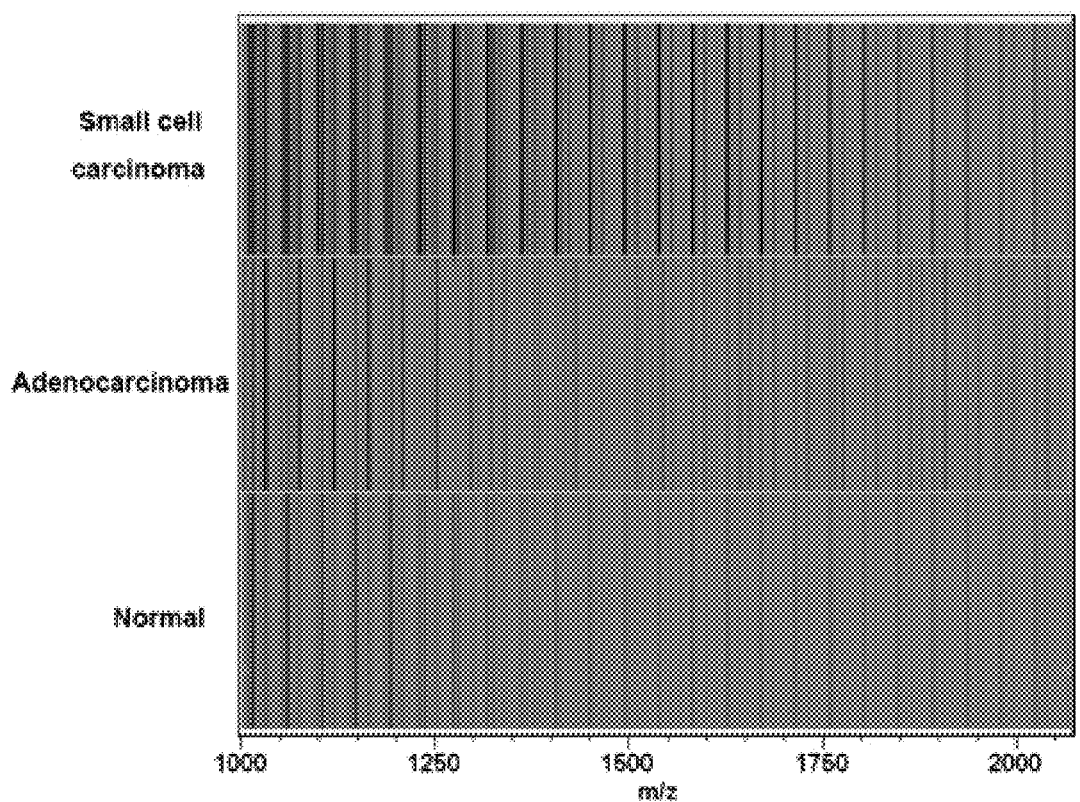
FIG. 6 shows a gel view of mass spectra of EBC of healthy subject (normal), adenocarcinoma and small cell patients analyzed by MALDI-TOF MS. Multiple polymer peaks were observed in all these samples.

To explore peptide biomarkers, the peptide components of EBC were first analyzed by MALDI-TOF MS. The results revealed that multiple polymer peaks were the major signals in mass spectra (FIG. 6). Thus, we checked the polypropylene collector of EcoScreen condenser and the assigned wash material Descogen to trace the contaminants. After MS analysis, the multiple polymer signals were confirmed coming from the released materials of polypropylene collector and the trace amounts of detergent Descogen. To avoid the interference of polymers and to remove these contaminants, EBC samples were further subjected to the purification by affinity beads. Three kinds of magnetic bead, $C_{18}$, WCX (weak cation exchange) and Cu, were tested to purify EBC, and their effects on decreasing polymer contaminants were determined by MS analysis. The Cu magnetic bead showed a better removing effect than the others. Therefore, we chose Cu magnetic bead to perform the purification of EBC and the purified samples as starting materials were applied to nano-LC/LTQ-FTICR MS for peptide identification.

Before MS analysis, EBC was purified by using metal-affinity copper magnetic beads (ClinProt™, Bruker Daltonics, Leipzig, Germany). First, EBC was dried by speed-vac and then re-dissolved in 10 µl $H_2O$ (containing 0.1% TFA). The purification procedure went through three steps, binding, washing and elution, according to the manufacturer's protocol. Briefly, 2.5 µl copper magnetic beads were washed and re-suspended in 20 µl binding buffer. Then 10 µl EBC solution was added and mixed carefully by pipetting up and down ten times, followed by the separation of unbound solution using a magnetic bead separator. After washing two times, the bound peptides and proteins were eluted with 6 µl elution buffer and immediately stored at −20° C. until MS assay.

Example 3

MALDI-TOF MS Analysis

For MALDI-TOF MS analysis, we mixed 1 µl purified EBC with 1 µl matrix solution consisting of 2,5-dihydroxy-benzoic acid (50 nmol/µl in 50% ACN) and 0.4% phosphoric acid. Then 1 µl of the resulting mixture was spotted onto MALDI stainless steel sample plate and allowed to air dry at room temperature. Measurements were performed on an Ultraflex II MALDI-TOF/TOF mass spectrometer (Bruker Daltonik GmbH, Bremen, Germany). Mass spectra were obtained in the range of mass to charge ratio (m/z) from 1,000 to 10,000.

Example 4

Nano-LC/LTQ-FTICR MS Analysis

Purified EBC was separated by a nano-chromatographic system with an Agilent 1100 Series binary HPLC pump (Agilent Technologies, Palo Alto, Calif.), a Famos autosampler (LC Packings, San Francisco, Calif.), a self-packed pre-column (150 μm I.D.×20 mm) and a reverse phase C18 column (75 μm I.D.×300 mm), which used the Magic $C_{18}AQ$ resin (particle size, 5 μm; pore size, 200 Å; Michrom Bioresources, California, USA). Chromatographic separation was achieved at split flow rate 300 nl/min by using 0.1% formic acid in water as mobile phase A and 0.1% formic acid in 80% acetonitrile as mobile phase B in a 60 min running cycle. MS experiments were performed with a LTQ-FTICR MS (Thermo Electron, California, USA) equipped with an electrospray ion source (New Objective, Massachusetts, USA). The full-scan mass survey (m/z 320-1,800) was executed in FTICR MS with mass resolution of 100,000 at m/z 400. When their intensities were above a minimum threshold of 1,000 counts, the parent ions were selected for MS/MS analysis. Singly charged ions were rejected from MS/MS sequencing.

Example 5

Mass Data Analysis and Peptide Constituents of EBC

The .RAW files of spectra were converted to MGF files with Mascot Daemon (data import filter: mass range, 600-5,400) and searched by the MASCOT (version 2.1, Matrix Science Ltd., London, UK) software platform based on the Swiss-Prot protein database. The following MASCOT parameter settings were used: the peptide tolerance was 15 ppm with $2^+$ and $3^+$ peptide charges, and the MS/MS tolerance was 0.6 Da. No enzyme cleavage and modification were chosen. The significance threshold for the identification was set to p<0.01.

Figure 7:
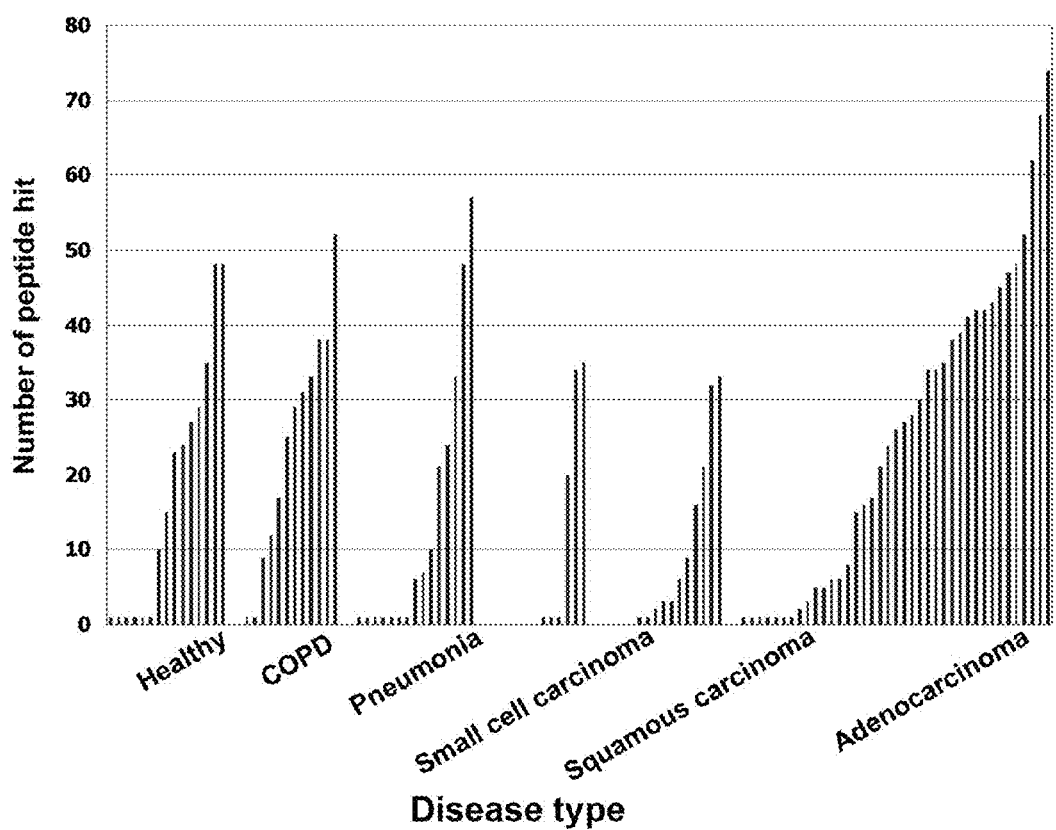
FIG. 7 shows the numbers of peptide hits for keratin type I cytoskeletal 9 and type II cytoskeletal 1 in individual EBC samples of different disease types.

Based on MS/MS analysis and MASCOT search, approximately 20 to 100 peptides in each EBC sample were identified. There were fewer than ten proteins deduced from the identified peptides in every EBC sample. Total twenty kinds of deduced protein were found in all EBC samples (FIG. 5). Among the identified peptides, the most abundant peptides were the fragments of keratin type I cytoskeletal 9 and type II cytoskeletal 1. The hit number of peptides of both proteins showed no obvious difference in various groups of EBC (FIG. 7). The mass peak-area intensities of relative peptides of both proteins also showed no difference. Most identified peptides did not consistently express in the specific disease type or in every EBC sample. Only one exception was the dermcidin-derived peptide.

Example 6

Dermcidin Peptide E-R11 Serves as NSCLC Biomarker

The 564.76 m/z DCD peptide with charge state +2 had a conspicuous MS/MS spectrum (FIG. 2A) for sequence determination, which was ENAGEDPGLAR (named E-R11; SEQ ID NO: 2) corresponding to with amino acid residues 43-53 of dermcidin (FIG. 2B). The mass peak-area intensities of E-R11 in every EBC sample was calculated by Xcalibur Qual Browsers version 1.4 SR1 program (FIG. 3). The results showed that EBC had higher levels of E-R11 in NSCLC group, including squamous carcinoma and adenocarcinoma, than healthy, SCLC and the other respiratory disease groups. The average mass peak-area intensities were 2.15×105 for squamous and 2.46×105 for adenocarcinoma, but only 3.21×104, 2.07×104, 4.54×104 and 4.06×104 for healthy subjects, COPD, pneumonia and small cell carcinoma, respectively. Therefore, E-R11 could serve as a potential biomarker to distinguish NSCLC from healthy and other lung disease statuses, including COPD and pneumonia. Nevertheless, E-R11 was not suitable for SCLC detection.

Example 7

Sensitivity and Specificity of E-R11 for Diagnosis of NSCLC

Based on the mass peak-area intensity distribution, two characteristic lines were drawn (FIG. 3). The first line with mass peak-area intensity $1.04 \times 10^5$ was the highest intensity of E-R11 in the healthy group. This cut-off threshold meant all healthy people would not be diagnosed with NSCLC, however, part of COPD and pneumonia patients could have false diagnoses. The specificities for healthy subjects, COPD and pneumonia patients were 100%, 91% and 86%, respectively, and for all non-cancer groups the specificity is 92%. With a cut-off value of $1.04 \times 10^5$, the sensitivities for squamous and adenocarcinoma patients were 50% and 63%, respectively, and 60% for all NSCLC groups. The second cut-off line with mass peak-area intensity $1.82 \times 10^5$ was the highest intensity of E-R11 in all non-cancer groups. With this cut-off value, the diagnosis specificity reached 100%. The sensitivity remained at 50% for squamous diagnosis, but it reduced to 44% for adenocarcinoma diagnosis. For all NSCLC groups the sensitivity was 45%.

Receiver operating characteristic (ROC) analysis was performed to determine an optimal diagnostic cut-off point (FIG. 4). Based on the mass peak-area intensity of E-R11, sensitivity and specificity were associated with the differentiation of NSCLC. The value of area under the curve (AUC) was 0.75 that illustrated E-R11 had a fair to good diagnostic power. The diagnostic sensitivity and specificity showed an optimum combination when the cut-off value of E-R11 mass peak-area intensity was approximately equal to $1 \times 10^5$. This value was similar to the aforementioned first line cut-off threshold that showed no false positive diagnosis for healthy people. Therefore, an E-R11 mass peak-area intensity of $1.04 \times 10^5$ was reasonable for outcome measurement.

Using E-R11 for the diagnosis of NSCLC, the sensitivity and specificity showed no notable difference between early and late cancer stages (FIG. 1). About 60% early stage NSCLC patients (squamous: 67% (2/3); adenocarcinoma: 60% (3/5)) can be diagnosed with cancer, that is E-R11 possesses valuable potential to serve as clinical biomarker for NSCLC early diagnosis.

Example 8

Quantitative Analysis of Peptide

Figure 8:
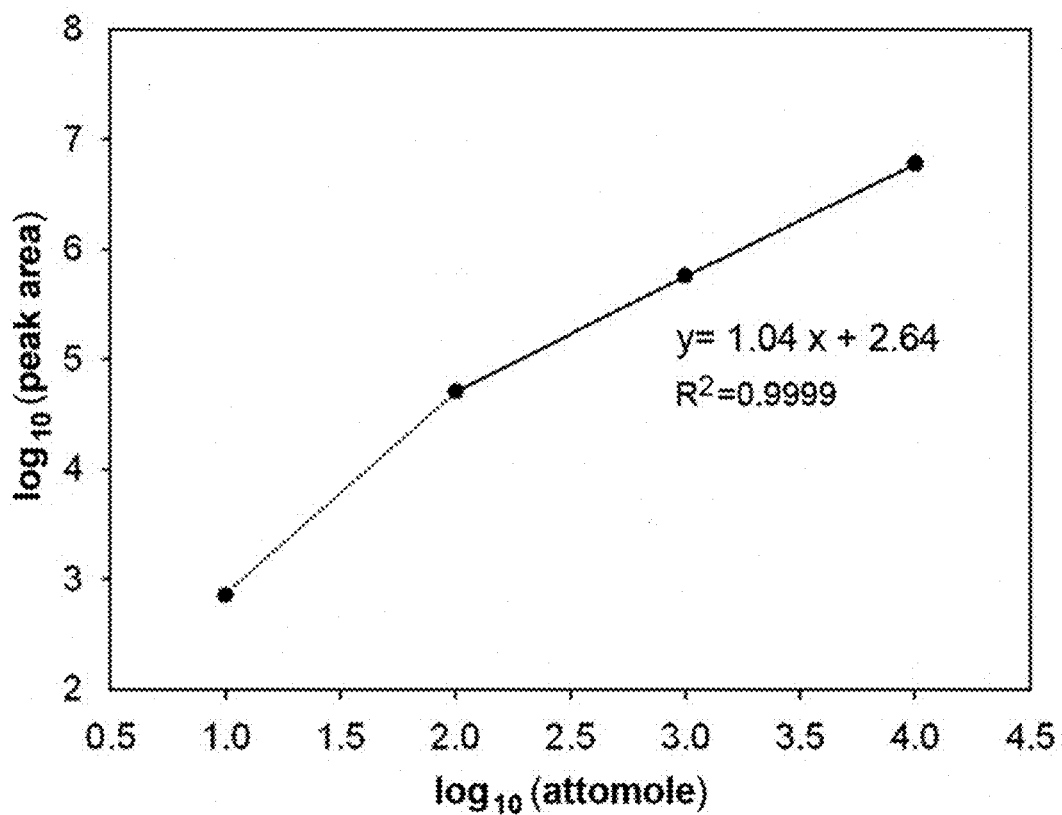
FIG. 8 shows quantitative calibration of E-R11. Synthetic E-R11 peptides with quantities of 10, 100, 1,000 and 10,000 attomoles respectively were analyzed by nano-LC/LTQ-FTICR MS, and the peak areas measured. The logarithm values of peptide quantity and peak-areas describe the plot by a linear function. Solid line: linear equation obtained by using three spots with quantity equal to or more than 100 attomoles. Dashed line: deviation from the linear equation.

To measure the E-R11 quantity in EBC, we used a synthetic peptide as a standard for quantitative calibration. The synthetic peptides from 10 to 10,000 attomoles were applied to MS analysis, and the peak-area intensities were measured. The peak-area intensity was calculated as the average value of three repeated experiments. The relationship of peptide quantity and peak-area intensity was described using a linear function (FIG. 8). By directly plotting chart with the spots of peptide quantity greater than 100 attomoles, a good linear relationship can be obtained that linear equation y=1.04x+2.64 with r-square=0.9999. The major deviation came from low levels of peptides because they cannot produce adequate signals. According to this linear equation, mass peak-area intensity $1.04 \times 10^5$ was equal to 196 attomoles.

DCD-derived peptide E-R11 having the sequence ENAGEDPGLAR (SEQ ID NO: 2) was synthesized by using the ABI 433A peptide synthesizer (Applied Biosystems, California, USA). Synthetic E-R11 peptide was subjected to LTQ-FTICR MS analysis at the desired concentration. The chromatographic peak area derived from mono-isotopic ions in FTICR MS scans was calculated by Xcalibur Qual Browsers version 1.4 SR1 program. The selected mass window of mono-isotopic ion was ±0.02 m/z.

Example 9

Validation of E-R11

Figures 2, 9:
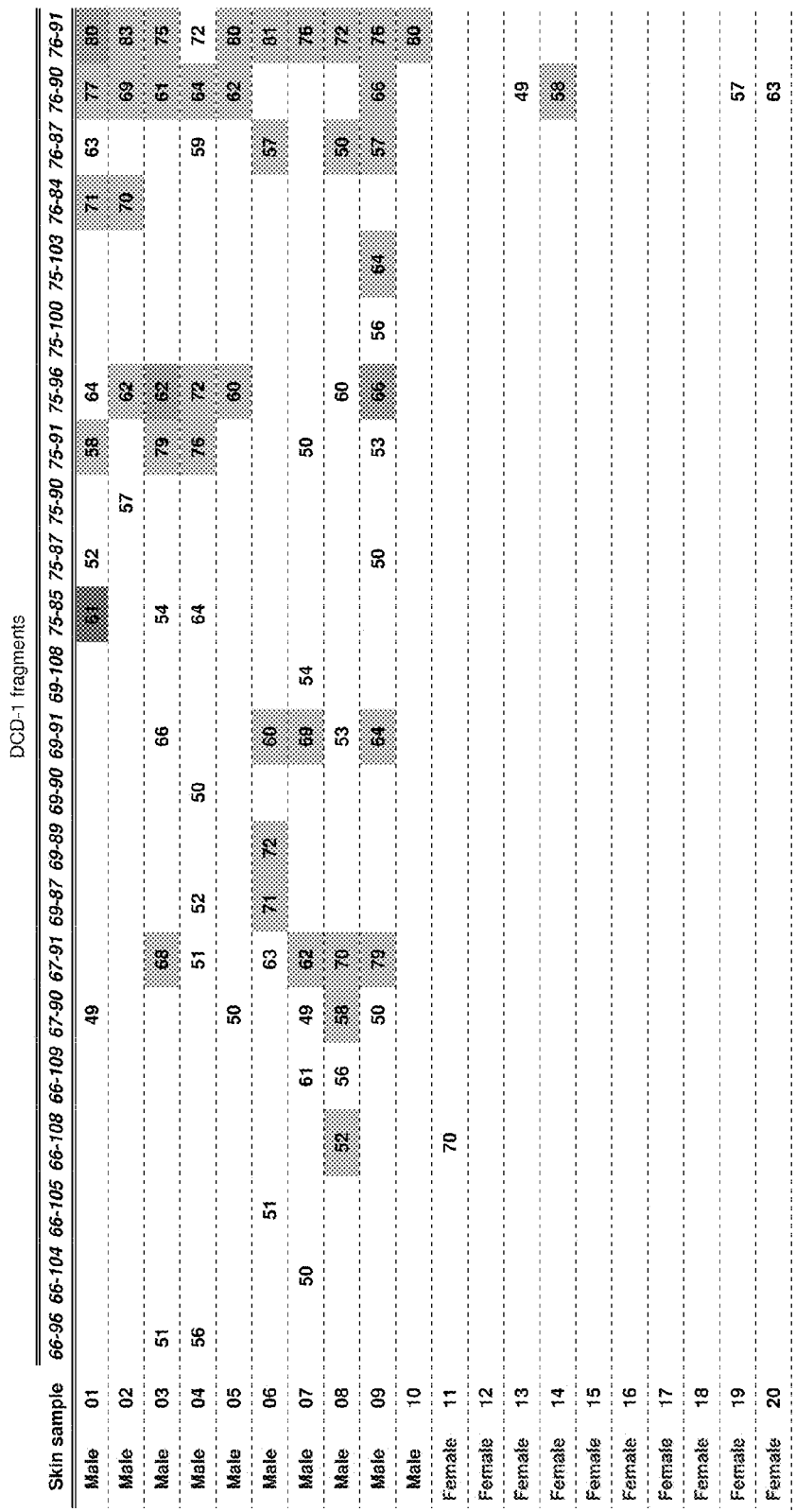
Figures 3, 9:
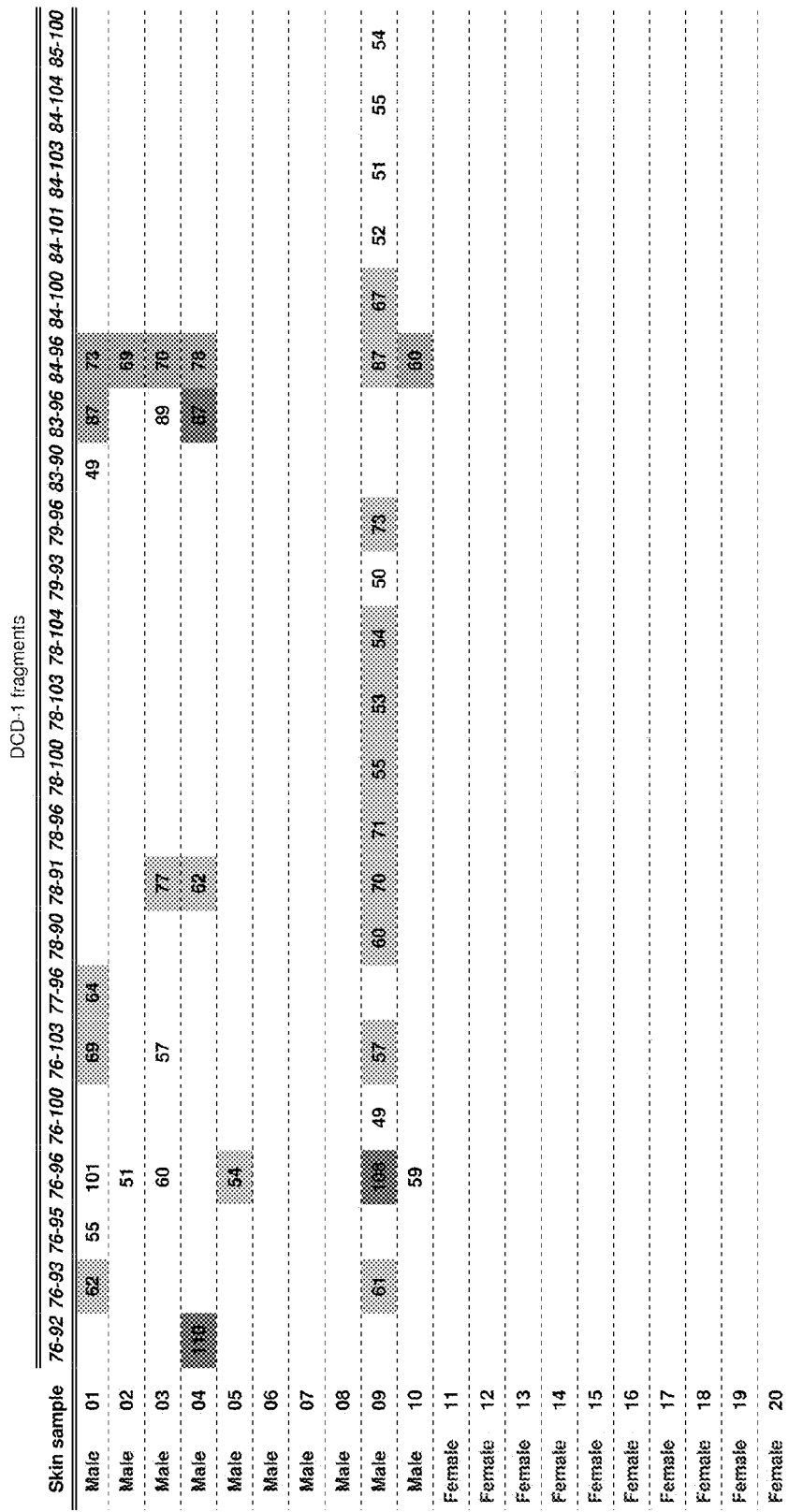

To eliminate the possibility that E-R11 peptides came from the contamination of skin contact during sample collection, we applied distilled water on the skins of subjects and then analyzed these extracted samples without enzymatic treatment. The results showed that the fragments of DCD-1 peptides were the major components in skin extracts although trace amount of E-R11 was also detected in 40% (8/20) samples (FIGS. 9-1 through 9-4). According to this observation, it was a reasonable speculation that if skin contamination occurred, DCD-1 peptide fragments would more easily be detected than E-R11. Actually the DCD-1 peptide fragments were not frequently detected as E-R11 in EBC samples. In addition, the EBC collection was randomized according to patient examination sequence. It is unlikely that contamination only occurred at NSCLC patients. Therefore, the possibility of skin contamination could be ruled out.

Figure 10:
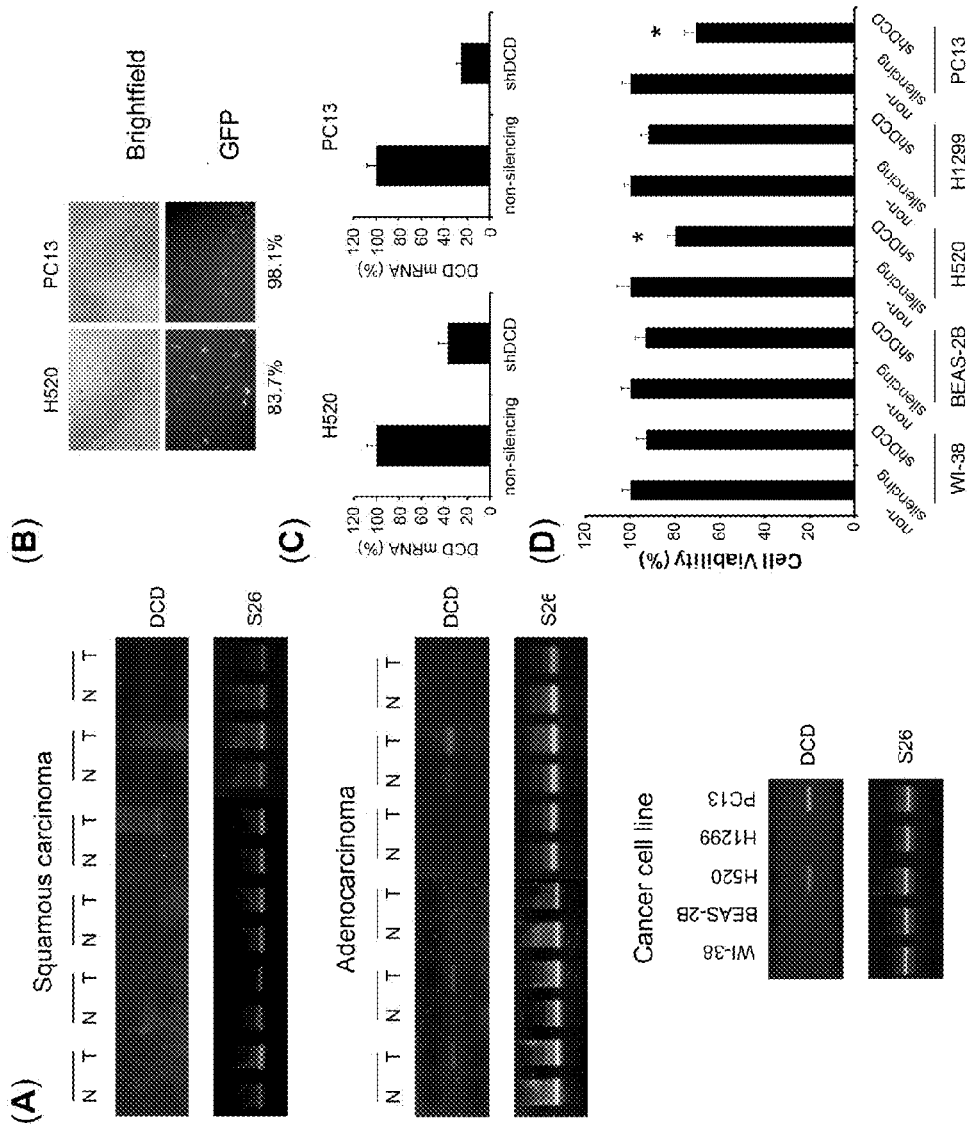
FIGS. 10A-10D show DCD endogenous expression in lung cancer cells and associated with cancer cell growth.

The endogenous expression of DCD in tissues of lung cancer patients and in lung cancer cell lines was determined (FIG. 10A). Two out of six squamous carcinoma and three out of six adenocarcinoma tissue samples showed DCD RNA expression by RT-PCR analysis. Most of the paired normal tissue samples were found with either no or very weak DCD expression. The endogenous expression of DCD were also found in lung cancer cell lines H520 (squamous carcinoma) and PC13 (adenocarcinoma). Lung fibroblast cell line WI-38 and bronchial epithelial cell line BEAS-2B were found without endogenous DCD expression. These results demonstrated that DCD expression is activated in lung cancer cells.

Example 10

Cell Culture

Human normal lung fibroblast cell line, WI-38, was cultured in MEM medium (GIBCO). Human squamous lung cancer cell line, H520, human large cell lung cancer cell line, H1299, and human lung adenocarcinoma cell line, PC13 were cultured in DMEM medium (GIBCO). Above mediums were supplemented with 10% fetal bovine serum, 2 mM L-glutamine, 100 units/ml penicillin, and 100 g/ml streptomycin. Human bronchial epithelial cell line, BEAS-2B, was cultured in the specific basal medium, BEBM, with all growth factors in the kit (Lonza, Valais, Switzerland). All cells were incubated at 37° C. with 5% $CO_2$.

Example 11

RNA Preparation and RT-PCR

RNA was prepared from cultured cells and clinical tissues of lung cancer patients by using Trizol reagent (Life Technologies, Paisley, UK) according to the manufacturer's instructions. Reverse transcription was performed in 20 μl reaction containing 50 mM Tris (pH 8.3), 40 mM KCl, 6 mM $MgCl_2$, 500 μM of each dNTP, 5 mM DTT, 1 μg oligo-dT, 5 μg RNA and 20 U enzyme. The condition of thermal cycler was set at 42° C. for 1 hr, followed at 70° C. for 10 min. cDNA products were then diluted to 0.1 μg/μl with DEPC-treated water. PCR primers were DCD forward primer 5'-ACTC-CAGCACACAGAAGCATGAG-3' (SEQ ID NO:3) and DCD reverse primer 5'-CAGCTTTTTTTGCTC-CGTCTAGG-3' (SEQ ID NO:4). PCR reactions contained 0.1 μg cDNA, 10 mM KCl, 2 mM $MgSO_4$, 20 mM Tris, 0.1% Triton X-100, 10 mM $(NH_4)_2SO_4$, 0.1 μg/mL BSA, 1 μM primer, and 0.5 U Taq polymerase (Yeastern Biotech Co. Ltd., Taipei, Taiwan) in 20 μL. The Reaction was performed under an optimized procedure: 94° C. for 4 min 30 sec, followed by 38 cycles at 94° C. for 1 min, 55° C. for 1 min and 72° C. for 1 min, then 72° C. for 10 min. PCR products were electrophoresed on 2% agarose gels and DNA were stained with ethidium bromide and visualized under UV illumination.

Example 12

DCD shRNA Lentivirus Production

Plasmid pGIPZ-DCD-shRNA encoding lentivirus expressing shRNA and two packaging vector pCMVΔR8.91 and pMD.G were obtained from the library of the National RNAi Core Facility (Taipei, Taiwan). Plasmids were purified using the QIAfilter Plasmid Kit (QIAGEN, Maryland, USA), then transfected into HEK 293T cells by calcium phosphate method to produce lentivirus (33). Viral packaging cell line, HEK 293T, was cultured to 50% confluence. The transfection reagents contained 7 μg of pGIPZ-DCD-shRNA, 7 μg of pCMVΔR8.91 and 1 μg of pMD.G. Viral soup was harvested after 48 hr and 72 hr culture.

Example 13

Biological Activity of DCD in Lung Cancer Cells

To characterize the biological activities of DCD in lung cancer cells, the functional consequences of DCD expression knockdown were determined using lentiviral vector delivered shRNA. Real-time quantitative PCR was used to assay the knockdown effects of DCD. Cells at a concentration of $2 \times 10^3$ cells/well were seeded into 96-well plate with 50 μl growth medium. For infection, 50 μl of viral soup containing 8 μg/ml polybrene was added to cultured cells. The plate was centrifuged at 37° C., 3,000 rpm for 15 min to enhance the infection efficiency. After 72 hr incubation, CellTiter-Glo assay (Promega, Wisconsin, USA) was used to detect cell viabilities.

The results indicated that both cell lines H520 and PC13 can be infected at high efficiency by DCD shRNA lentiviruses (FIG. 10B) and DCD shRNA can significantly knockdown the endogenous RNA expression of DCD in H520 (~70%) and PC13 (~80%) (FIG. 10C). We further examined whether DCD expression knockdown results in growth reductions in normal or cancer cell lines (FIG. 10D). The results showed 20 to 30 percent growth reductions in H520 and PC13 cells after DCD shRNA delivery, while there were no growth reductions in normal fibroblast and epithelial cells.

All publications and patent applications cited in this specification are incorporated herein by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

What is claimed is:

1. A method of determining the level of a peptide biomarker E-R11 consisting of the sequence ENAGEDPGLAR (SEQ ID NO: 2) in a test subject, the method comprising:
   (a) providing a sample obtained from an exhaled breath condensate (EBC) of the test subject, wherein the sample comprises the peptide biomarker E-R11; and
   (b) detecting a level of the peptide biomarker E-R11 in the sample obtained from the exhaled breath condensate, wherein the peptide biomarker E-R11 is a partial sequence of dermcidin (DCD; SEQ ID NO: 1).

2. The method of claim 1, wherein the test subject is suspected of having a lung cancer which is a non-small cell lung carcinoma (NSCLC) selected from squamous cell carcinoma, adenocarcinoma, large cell lung carcinoma, or any combination thereof.

3. The method of claim 1, wherein the peptide biomarker E-R11 is formed by enzymatic digestion of dermcidin.

4. The method of claim 1, wherein the level of the peptide biomarker E-R11 is detected by a method comprising mass spectrometry (MS).

5. The method of claim 4, wherein the mass spectrometry comprises matrix-assisted laser desorption/ionization time-of-flight mass spectrometry (MALDI-TOF MS).

6. The method of claim 4, wherein the mass spectrometry comprises linear ion trap-Fourier transform ion cyclotron resonance mass spectrometry (LTQ-FTICR MS).

7. The method of claim 4, wherein the mass spectrometry comprises surface-enhanced laser desorption ionization mass spectrometry (SELDI-MS).

8. The method of claim 1, wherein the sample comprises purified peptide constituents from ESC.

9. The method of claim 8, wherein the peptide constituents from EBC are purified using copper-coated magnetic beads.

10. The method of claim 1, wherein the level of the peptide biomarker E-R11 is detected by mass spectrometry and the peptide biomarker E-R11 level is measured as mass peak area intensity, wherein a mass peak-area intensity of $1.04 \times 10^5$ is equal to 196 attomoles.

11. The method of claim 10, wherein the level of the peptide biomarker E-R11 is measured as mass peak area intensity about $1.0 \times 10^5$ or above, wherein the mass spectrometry comprises surface-enhanced laser desorption ionization mass spectrometry (SELDI-MS).

12. The method of claim 10, wherein the level of the peptide biomarker E-R11 is measured as mass peak area intensity about $1.8 \times 10^5$, wherein the mass spectrometry comprises surface-enhanced laser desorption ionization mass spectrometry (SELDI-MS).

13. The method of claim 1, wherein the test subject has lung cancer and the method further comprises monitoring the inhibition of lung cancer growth following administration of a chemotherapeutic regimen, a surgical resection or a photodynamic therapy to the test subject.

14. The method of claim 13 wherein the chemotherapeutic regimen comprises a therapeutic dose of one or more of Cisplatin, Etoposide, Carboplatin, Paclitaxel, Docetaxel, Vinorelbine, Doxorubicin, Vincristine, Ifosfamide, and Gemcitabine.

* * * * *

SEQUENCE LISTING

<160> NUMBER OF SEQ ID NOS: 4

<210> SEQ ID NO 1
<211> LENGTH: 110
<212> TYPE: PRT
<213> ORGANISM: Homo sapiens
<300> PUBLICATION INFORMATION:
<308> DATABASE ACCESSION NUMBER: Uniprot / P81605
<309> DATABASE ENTRY DATE: 2002-01-23
<313> RELEVANT RESIDUES IN SEQ ID NO: (1)..(110)

<400> SEQUENCE: 1

Met Arg Phe Met Thr Leu Leu Phe Leu Thr Ala Leu Ala Gly Ala Leu
1               5                   10                  15

Val Cys Ala Tyr Asp Pro Glu Ala Ala Ser Ala Pro Gly Ser Gly Asn
            20                  25                  30

Pro Cys His Glu Ala Ser Ala Ala Gln Lys Glu Asn Ala Gly Glu Asp
        35                  40                  45

Pro Gly Leu Ala Arg Gln Ala Pro Lys Pro Arg Lys Gln Arg Ser Ser
    50                  55                  60

Leu Leu Glu Lys Gly Leu Asp Gly Ala Lys Lys Ala Val Gly Gly Leu
65                  70                  75                  80

Gly Lys Leu Gly Lys Asp Ala Val Glu Asp Leu Glu Ser Val Gly Lys
                85                  90                  95

Gly Ala Val His Asp Val Lys Asp Val Leu Asp Ser Val Leu
            100                 105                 110

<210> SEQ ID NO 2
<211> LENGTH: 11
<212> TYPE: PRT
<213> ORGANISM: Homo sapiens
<300> PUBLICATION INFORMATION:
<308> DATABASE ACCESSION NUMBER: Uniprot / P81605
<309> DATABASE ENTRY DATE: 2002-01-23
<313> RELEVANT RESIDUES IN SEQ ID NO: (43)..(53)

<400> SEQUENCE: 2

Glu Asn Ala Gly Glu Asp Pro Gly Leu Ala Arg
1               5                   10

<210> SEQ ID NO 3
<211> LENGTH: 23
<212> TYPE: DNA
<213> ORGANISM: Artificial Sequence
<220> FEATURE:
<223> OTHER INFORMATION: Synthetic sequence

<400> SEQUENCE: 3
actccagcac acagaagcat gag                                                23

<210> SEQ ID NO 4
<211> LENGTH: 23
<212> TYPE: DNA
<213> ORGANISM: Artificial Sequence
<220> FEATURE:
<223> OTHER INFORMATION: Synthetic sequence

<400> SEQUENCE: 4
cagctttttt tgctccgtct agg                                                23